US012646606B2

(12) United States Patent
Collins

(10) Patent No.: US 12,646,606 B2
(45) Date of Patent: Jun. 2, 2026

(54) SYSTEM AND METHOD FOR MAPPING A PATIENT INTERACTION/INFORMATION INTO A VISUAL REPRESENTATION AND REVIEW INTERFACE IN ORDER TO MAP A PATIENT INTERACTION/INFORMATION TO A PATIENT ANATOMY

(71) Applicant: ChartLamp International, Inc, Vancouver, WA (US)

(72) Inventor: Justin Collins, Vancouver, WA (US)

( * ) Notice: Subject to any disclaimer, the term of this patent is extended or adjusted under 35 U.S.C. 154(b) by 412 days.

(21) Appl. No.: 18/129,349

(22) Filed: Mar. 31, 2023

(65) Prior Publication Data

US 2024/0331845 A1 Oct. 3, 2024

(51) Int. Cl.
| | |
|---|---|
| *G16H 10/60* | (2018.01) |
| *G06F 3/038* | (2013.01) |
| *G16H 30/40* | (2018.01) |
| *G16H 50/20* | (2018.01) |
| *G16H 50/30* | (2018.01) |
| *G16H 15/00* | (2018.01) |

(52) U.S. Cl.
CPC ............. *G16H 30/40* (2018.01); *G06F 3/038* (2013.01); *G16H 50/20* (2018.01); *G16H 50/30* (2018.01)

(58) Field of Classification Search
CPC .. G06F 3/038; G06F 16/90335; G06F 3/0482; G06F 3/04842; G06F 3/0488; G06F 30/40; G06F 40/63; G16H 10/60; G16H 15/00; G16H 30/40; G16H 50/20; G16H 50/30; G16H 50/50; G16H 50/70; G16H 30/20; G16H 70/60; G16H 80/00; G16H 40/20
USPC ................................................... 382/128–130
See application file for complete search history.

(56) References Cited

U.S. PATENT DOCUMENTS

| | | | | |
|---|---|---|---|---|
| 11,145,395 | B1 * | 10/2021 | Mitchell ................ | G16H 40/67 |
| 2005/0134609 | A1 * | 6/2005 | Yu ........................... | G16H 40/63 |
| | | | | 345/629 |
| 2014/0100885 | A1 * | 4/2014 | Stern ...................... | G16H 50/30 |
| | | | | 705/3 |
| 2014/0164968 | A1 * | 6/2014 | Aalami ................. | G06F 3/0488 |
| | | | | 715/771 |
| 2018/0247701 | A1 * | 8/2018 | Vandersluis ........... | G16H 10/60 |
| 2023/0368878 | A1 * | 11/2023 | Molenda ................ | G16H 70/60 |

* cited by examiner

*Primary Examiner* — Chad Dickerson
(74) *Attorney, Agent, or Firm* — Mohamed C. Azeez

(57) ABSTRACT

A method for an interactive medical record review, said method comprising the steps of: displaying at-a-glance anatomical imagery with health code and/or date of event associated with a patient interaction on a whole-body graphic; and configuring the anatomical imagery on the whole-body graphic for pointing-device control enabling a requester to access and interact with the code-standardized data related to the patient interaction.

15 Claims, 10 Drawing Sheets

Anteroposterior (AP) radiographs showing an atypical femoral shaft fracture pre-operatively from the same individual. Note the oblique and transverse components (white arrows) and a medial "spike" (black arrow) on the preoperative.

receiving at least one medical billing code with respect to a patient;

52 associating the medical billing code with an anatomical image;     54 rendering the anatomical image onto the patients body map.

56

Anteroposterior (AP) radiographs showing an atypical femoral shaft fracture pre-operatively from the same individual. Note the oblique and transverse components (white arrows) and a medial "spike" (black arrow) on the preoperative.

| Plaintiff: John Doe | Event: Car Accident |
|---|---|
| Insurance: GEICO | Date of Loss: 3-15-2022 |

2022-A3370

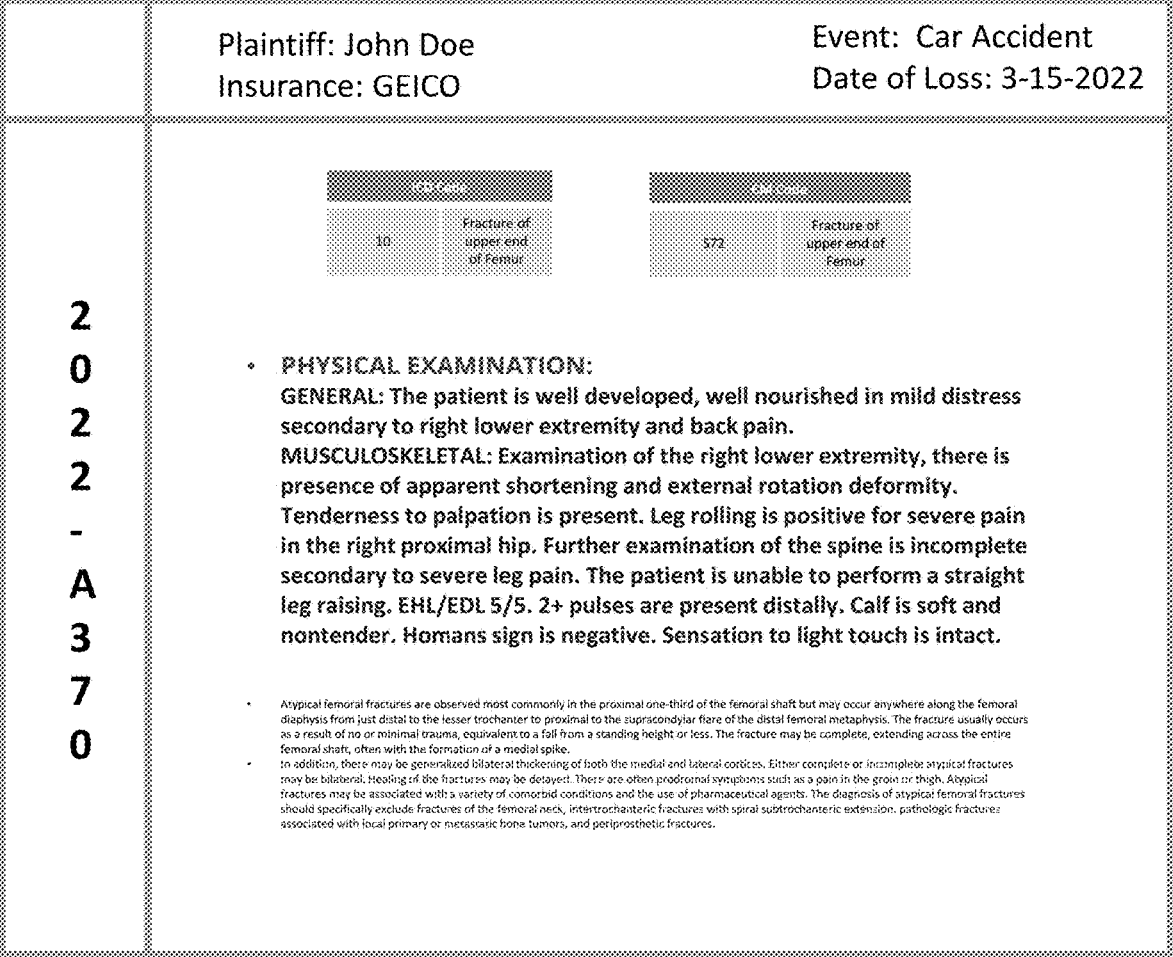

- PHYSICAL EXAMINATION:
  GENERAL: The patient is well developed, well nourished in mild distress secondary to right lower extremity and back pain.
  MUSCULOSKELETAL: Examination of the right lower extremity, there is presence of apparent shortening and external rotation deformity. Tenderness to palpation is present. Leg rolling is positive for severe pain in the right proximal hip. Further examination of the spine is incomplete secondary to severe leg pain. The patient is unable to perform a straight leg raising. EHL/EDL 5/5. 2+ pulses are present distally. Calf is soft and nontender. Homans sign is negative. Sensation to light touch is intact.

- Atypical femoral fractures are observed most commonly in the proximal one-third of the femoral shaft but may occur anywhere along the femoral diaphysis from just distal to the lesser trochanter to proximal to the supracondylar flare of the distal femoral metaphysis. The fracture usually occurs as a result of no or minimal trauma, equivalent to a fall from a standing height or less. The fracture may be complete, extending across the entire femoral shaft, often with the formation of a medial spike.
- In addition, there may be generalized bilateral thickening of both the medial and lateral cortices. Either complete or incomplete atypical fractures may be bilateral. Healing of the fractures may be delayed. There are often prodromal symptoms such as a pain in the groin or thigh. Atypical fractures may be associated with a variety of comorbid conditions and the use of pharmaceutical agents. The diagnosis of atypical femoral fractures should specifically exclude fractures of the femoral neck, intertrochanteric fractures with spiral subtrochanteric extension, pathologic fractures associated with local primary or metastatic bone tumors, and periprosthetic fractures.

FIG. 10

SYSTEM AND METHOD FOR MAPPING A PATIENT INTERACTION/INFORMATION INTO A VISUAL REPRESENTATION AND REVIEW INTERFACE IN ORDER TO MAP A PATIENT INTERACTION/INFORMATION TO A PATIENT ANATOMY

BACKGROUND

Field

This invention relates generally to medical records review, and more specifically, to an automated system and method for visualizing patient medical records.

Related Art

In today's litigious environment, personal injury claims are becoming increasingly common, with the United States Department of Justice reporting approximately 400,000 claims filed every year in the United States alone. The success of these claims by claimants and their defense by insurance companies hinges on the establishment of personal injuries sustained in an accident, their severity and their estimated cost of repair, which is primarily determined through medical records. While obtaining these records is essential for interested parties, balancing access with patient privacy is of paramount importance.

Medical record retrieval, summarization, and review is a tedious and time-consuming process that requires a comprehensive understanding of medical documentation. Retrieving accurate information from these records is critical for personal injury claims, as it can impact the outcome of the case. With multiple parties involved in the retrieval process, including healthcare providers and legal representatives, navigating the various reporting requirements can be challenging. Moreover, the sensitivity of medical records means that strict protocols must be followed to ensure patient privacy.

To address these challenges, many attorneys now use secure online portals like ShareScape™ to receive their clients' medical records from healthcare providers. These portals offer a single-access point to patients' medical records, enabling parties to securely access patient and case records with third-party integrations. ShareScape™ offers keyword search functionalities, annotation tools, shareable capabilities, and record storage to make the retrieval process more time-efficient.

However, despite these benefits, issues remain. The learning curve associated with navigating the portal's dashboard can be steep, causing frustration and increasing the time involved in retrieving medical records. As a result, there is a significant need for a more robust, comprehensive, one-stop summarization and review solution that compiles patient health data and renders it into a graphical-based, easy-to-use interactive summary.

The benefits of such a system are many. A predominantly visual layer that selectively accesses information from the patient case history based on quick-at-a-glance cursor control features will undoubtedly focus attention on the most important issues and reduce the frustration associated with the retrieval process. An automated system capable of visually mapping standardized health codes would benefit all stakeholders involved in the medical records review process, reducing the time and effort involved in targeted medical records retrieval. Such a system would compile relevant health data related to an individual, including encounters, testing, treatments, procedures, health code, prescriptions and more, hereinafter referred to as "interaction(s)".

The CURES ACT, passed in 2016, aims to streamline and modernize the retrieval of medical records by mandating that healthcare providers provide patients with access to their electronic health records (EHRs) in a timely manner and at a reasonable cost. This provision allows patients to share their records with whomever they choose, including attorneys and other stakeholders in personal injury claims. Additionally, EHRs can be accessed and shared through the use of third-party integrations like ShareScape™, further simplifying the process.

However, even with EHRs and specialized document retrieval services like ShareScape™, retrieval, mapping, and reviewing medical records is still a tedious and time-consuming process. Electronic health records (EHRs) can be difficult to share and exchange between different systems due to a lack of standardization and interoperability. This can lead to data silos where patient information is inaccessible or difficult to access, making it challenging to provide coordinated and comprehensive care. Furthermore, access to EHRs is typically restricted to authorized personnel who have been trained on how to use the system and understand patient privacy laws. Legal staff may not have the necessary credentials or training to access or interact with her databases. As a result, they may face challenges in accessing relevant patient information for legal purposes.

However, there are efforts underway to improve EHR interoperability and make it easier to share patient data between different systems. For example, the Office of the National Coordinator for Health Information Technology (ONC) has established standards and certification criteria for EHRs to promote interoperability and data exchange. Additionally, health information exchanges (HIEs) are being developed to facilitate the secure sharing of patient information between healthcare providers, payers, and other stakeholders. While these efforts are earnestly ongoing, they don't do enough for improving the accessibility and usability of EHRs for legal staff and other stakeholders in the medical record retrieval space.

A comprehensive, efficient, and user-friendly medical record review system that compiles all pertinent data into a graphical-based, interactive summary would significantly reduce the time and effort involved in understanding targeted medical records. Such a system would benefit all stakeholders involved by reducing the time and effort involved in identifying relevant information from a swath of text-rich cases composed of disparate health code regimes.

The implementation of such a system would improve the efficiency of the claim resolution process, reduce the burden on all parties involved, and ultimately result in better outcomes for patients and more efficient use of resources across the healthcare system. With the CURES ACT in place, a visually-aided and streamlined medical record review process that saves time for all stakeholders is urgently needed.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Embodiments disclosed include a system and method for mapping patient information/interaction for claim submission or reimbursement—or for any medical record review purpose. In one embodiment, the system and method involve receiving information of at least one code from any one of a health code regime with respect to an individual patient and matching the code(s) with an image or icon representing an anatomy and/or physiology treated during the interaction. The image or visual interpretation of the interaction for the patient is then rendered onto an anatomical map as a first layer. The first layer may also include a timestamp of the interaction or a timeline of previous interactions. In yet other embodiments, the system and method allow for accessing at least a second graphical and/or informational layer for further detail related to the implicated interaction based on a pointing device control. The graphical layer may present at least one of a textual or numerical description with a related graphic further detailing the interaction. The informational layer presents at least one of a textual or numerical description without a related graphic further detailing the interaction or event.

In one embodiment, pointing device features may enable users to selectively access layers of information by at least one of hovering, extended press, right or left click, single-click, delayed double-click, touch, extended touch, double-touch, swiped, pinched, hand-gestured, or voice-activated. The method also includes a pointing device control enabling a user to quick double-click over a preview tile for routing to the corresponding layer.

In one embodiment, the system and method may also involve a split-screen visual display, where each screen represents a different layer, and each screen is modifiable in terms of sizing and position on the screen display. Additionally, electronic-discovery tools may be available for tagging the received patient interaction information for downstream analytic and provisioning purposes.

The patent claims also include a system for generating an interactive body map of a patient medical history, comprising a processor, a non-transitory storage element coupled to the processor, and encoded instructions stored in the non-transitory storage element. When implemented by the processor, the instructions configure the system to receive information of at least one code implicated from any one of a health code regime with respect to a patient's healthcare interaction, match the code with an image representing an anatomy and/or physiology treated during the interaction, and render the image onto an anatomical map of the patient as a first layer for selective information grabs.

The system also allows for accessing at least a second graphical and/or informational layer for further detail related to the interaction based on a pointing device control. The system may further include a visual layer module and a pointing device control module, which enables the user to access additional information or action by quick double-click over a preview tile for routing to either an informational or graphical layer. This system improves the medical record retrieval process by providing an easy-to-use and easy-to-read graphical interface for quicker and more efficient retrieval of patient data. The visual mapping of medical health codes onto anatomical maps allows users to quickly identify the implicated interaction or visit, and access further details using the graphical and informational layers. This system is suitable for use in claims submission/reimbursal or any other medical retrieval purposes.

Overall, the system/method for interactive medical record review includes two steps: displaying at-a-glance anatomical imagery with health code information on a whole-body graphic. In this step, the system/method allows the requester to get an overview of the patient's medical record at a glance. The health code information enables the requester to quickly identify the codes associated with the patient interaction. Step 2 configures the anatomical imagery on the whole-body graphic for pointing-device control, enabling a requester to access and interact with the code-standardized data related to the patient interaction. In this step, the system/method configures the anatomical imagery on the whole-body graphic for pointing-device control. This enables the requester to access and interact with the code-standardized data related to the patient interaction. The requester can use the pointing-device to click on the anatomical imagery, which will bring up the code-standardized data related to that part of the body. The requester can then interact with the data, such as adding notes, updating the patient's medical record, generating a report, coding, tagging, and, or sharing with relevant parties in a reporting/review/claims submission environment. This system/method provides an interactive and intuitive way for requesters to retrieve and interact with code-standardized data related to a patient's medical record.

Other embodiments include aspects corresponding to computer systems, apparatus, and computer programs recorded on one or more computer storage devices, each configured to perform the actions of the methods.

BRIEF DESCRIPTION OF THE DRAWINGS

The drawings illustrate the design and utility of embodiments of the present invention, in which similar elements are referred to by common reference numerals. In order to better appreciate the advantages and objects of the embodiments of the present invention, reference should be made to the accompanying drawings that illustrate these embodiments. However, the drawings depict only some embodiments of the invention, and should not be taken as limiting its scope. With this caveat, embodiments of the invention will be described and explained with additional specificity and detail through the use of the accompanying drawings in which:

FIG. 10 illustrates an exemplary schematic of at least a second layer of the health interaction mapping system in accordance with an aspect of the invention.

DETAILED DESCRIPTION

Figure 1A:
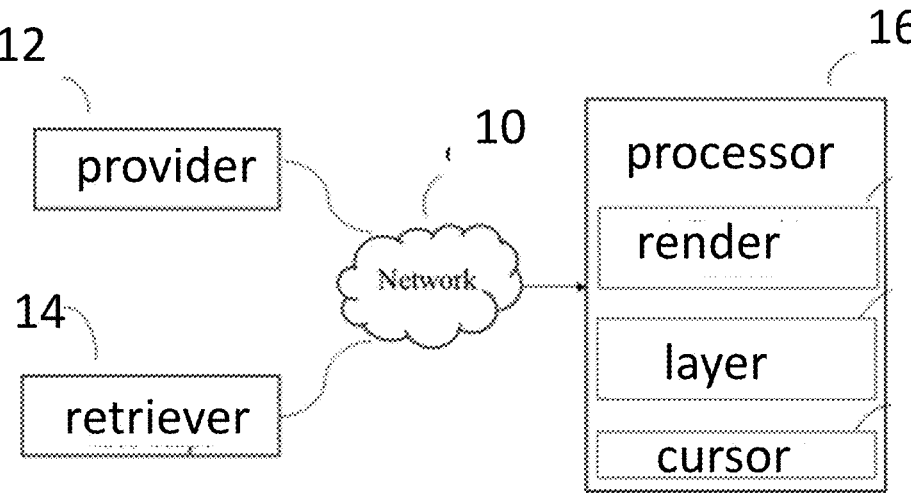
FIG. 1A illustrates a network diagram of the health interaction mapping system in accordance with an aspect of the invention.

In the following description, for purposes of explanation, numerous specific details are set forth in order to provide a thorough understanding of the invention. It will be apparent, however, to one skilled in the art that the invention can be practiced without these specific details. These embodiments are provided so that this disclosure will be thorough and complete, and will fully convey the scope of the disclosure to those skilled in the art.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

Glossary of Key Terms

HEALTH CODE: Health codes, including but not limited to medical health codes, is a standard to represent concepts in an unambiguous manner between a sender and receiver of information, a fundamental requirement for effective communication. Health information systems that communicate with each other rely on code sets/regimes and classification systems to represent health concepts. Some common code regimes currently used in the marketplace include: CPT (Current Procedural Terminology), HPCPS (Healthcare Common Procedure Coding System), ICD (The International Statistical Classification of Diseases and Related Health Problems), Logical Observation Identifiers Names and Codes (LOINC®), National Drug Code (NDC), RadLex, RxNorm, Systematized Nomenclature of Medicine-Clinical Terms (SNOMED-CT), Vaccines Administered (CVX), Manufacturers of Vaccines (MVX), United code for Units of Measure, and others—just to name a few.

INTERACTION: all relevant health data related to an individual, including encounters, testing, data aggregation, device data collection, treatments, procedures, prescriptions, associated health/health codes, and more, hereinafter referred to as "interaction", "health interaction", or "patient interaction".

REVIEW: any and all engagement with a medical record review/retrieval system for Various actors such as healthcare providers, insurance adjusters, legal professionals, and medical specialists utilize these systems for different reasons, including treatment, insurance claims evaluation, legal cases, and expert medical opinions.

Requesters: Healthcare providers, Insurance professions, legal professionals, the patient/individuals for example, doctors, nurses, and hospital staff use medical records retrieval systems to: access patient records for treatment purposes; update patient records with new information or test results; share patient records with other healthcare providers for coordinated care; retrieve historical data to inform clinical decision-making.

Insurance adjusters: Insurance adjusters use medical records retrieval systems to: collect patient records to evaluate insurance claims; verify medical treatments and services provided to claimants; detect fraudulent claims by comparing medical records to claim details.

Legal professionals: Legal professionals such as attorneys, paralegals, and legal assistants use medical records retrieval systems to: collect patient records for legal cases, such as personal injury or malpractice lawsuits; analyze medical records to determine liability and damages; prepare legal arguments and evidence based on medical records.

Patient/Individuals: Any individual at subject of the health interaction may request records for personal reasons, or for complying with an employer request, insurance coverage request, etc.

Specific embodiments of the invention will now be described in detail with reference to the accompanying FIGS. 1A-10. In the following detailed description of embodiments of the invention, numerous specific details are set forth in order to provide a more thorough understanding of the invention. In other instances, well-known features have not been described in detail to avoid obscuring the invention.

FIG. 1A illustrates a network diagram of the code mapping/visualizing system. The networked environment includes provider module 12, a retriever module 14 and a processing unit 16. The provider module 12, the retriever module 14 and the processing unit 16 are communicatively coupled through a network 10. Typically, the processing unit 16 enables the providers of patient interaction/s information to provide this data in order for a retriever/requester to access and interact with a visual and info-graphic rendering of provided patient data by the processor 16.

The system compiles all relevant health data related to an individual, including encounters, testing, data aggregation, device data collection, treatments, procedures, prescriptions, associated health/health codes, and more, hereinafter referred to as "interaction", "health interaction", or "patient interaction".

In an exemplary embodiment, the network 10 facilitates communication between a processor 16, a retriever, and a provider of patient data, with the processor 16 featuring render, layer, and cursor modules. The retriever module 14 retrieves patient data and information related to healthcare interactions and visits, including for visually-aided notes, diagnosis, recommendations, prescribed treatment, interactive maps and timelines, based on provider-uploaded patient data from the provider module 12 and processor-rendered visual/info-graphic layering, with the network 10 facilitating this communication. The processor 16 processes the provider 12 data and generates a visual representation of the interaction or visit onto an anatomical map as the first layer of information for retrievers. An intuitive UX/UI system allows users to navigate the graphical and informational layers. This system provides a quick and efficient way to retrieve patient data by visually mapping medical health codes onto anatomical maps, suitable for use in medical record retrieval purposes, including claims submission.

Examples of the providers include, but are not limited to, a healthcare provider, a hospital, a health monitoring service, a doctor, a physician, a clinician, a caregiver and a social service, or a service provider that specializes in continuously collecting medical data from patients and distributing the medical data to a plurality of concerned parties. Additionally, in some embodiments, providers may constitute real-time uploading of body worn devices typically embedded/equipped with one or more motion sensors, physiological sensors and environmental sensors. Examples of these sensors include, but are not limited to accelerometers, gyroscopes, inclinometers, geomagnetic sensors, global positioning systems, impact sensors, microphones, cameras, heart rate monitors, pulse oximeters, blood alcohol monitors, respiratory rate sensors, transdermal sensors, galvanic skin response (GSR) sensors and electromyography (EMG) sensors. In an embodiment of the present invention, the data captured by the one or more sensors is sent to the processing unit 16 and, or the provider module 12 through the network 10. Typically, the body worn device is worn on one or more body parts of the patient, such as wrist, waist, neck, arm, leg, abdomen, chest, thigh, head, ear and fingers. Further, the body worn device may be a wristband, a watch, an armband, a necklace, a headband, an earring, a waist belt and a ring. The body worn device communicates with the mobile communication device (including, but not limited to, a smartphone, a tablet, a personal digital assistant (PDA), thin-client, and a mobile phone) over a short-range wireless communication medium. Examples of the short-range wireless communication medium include Bluetooth, ZigBee, Infrared, Near Field Communication (NFC) and Radio-frequency identification (RFID).

Examples of retrievers or requesters include, but are not limited to, healthcare providers, including doctors, nurses, and other proxy healthcare professionals, requiring access to medical records to provide appropriate care to patients. Additionally, patients have the right to access their medical records and review their health information. Insurance companies may need access to medical records to process claims and determine coverage. Legal professionals, such as lawyers and paralegals, may need access to medical records for legal proceedings, including personal injury cases. Researchers require access to medical records to conduct studies and analyze health data. Government agencies, such as the Centers for Disease Control and Prevention (CDC) or the National Institutes of Health (NIH), may need access to medical records for public health research and surveillance. Finally, employers may also need access to medical records for employee health and wellness programs or to comply with employment regulations.

In continuing reference to FIG. 1A, the network 10 may be any suitable wired network, wireless network, a combination of these or any other conventional network, without limiting the scope of the present invention. Few examples may include a LAN or wireless LAN connection, an Internet connection, a point-to-point connection, or other network connection and combinations thereof. The network 10 may be any other type of network that is capable of transmitting or receiving data to/from host computers, personal devices, mobile phone applications, video/image capturing devices, video/image servers, or any other electronic devices. Further, the network 10 is capable of transmitting/sending data between the mentioned devices. Additionally, the network 10 may be a local, regional, or global communication network, for example, an enterprise telecommunication network, the Internet, a global mobile communication network, or any combination of similar networks. The network 10 may be a combination of an enterprise network (or the Internet) and a cellular network, in which case, suitable systems and methods are employed to seamlessly communicate between the two networks. In such cases, a mobile switching gateway may be utilized to communicate with a computer network gateway to pass data between the two networks. The network 10 may include any software, hardware, or computer applications that can provide a medium to exchange signals or data in any of the formats known in the art, related art, or developed later.

Figure 1B:
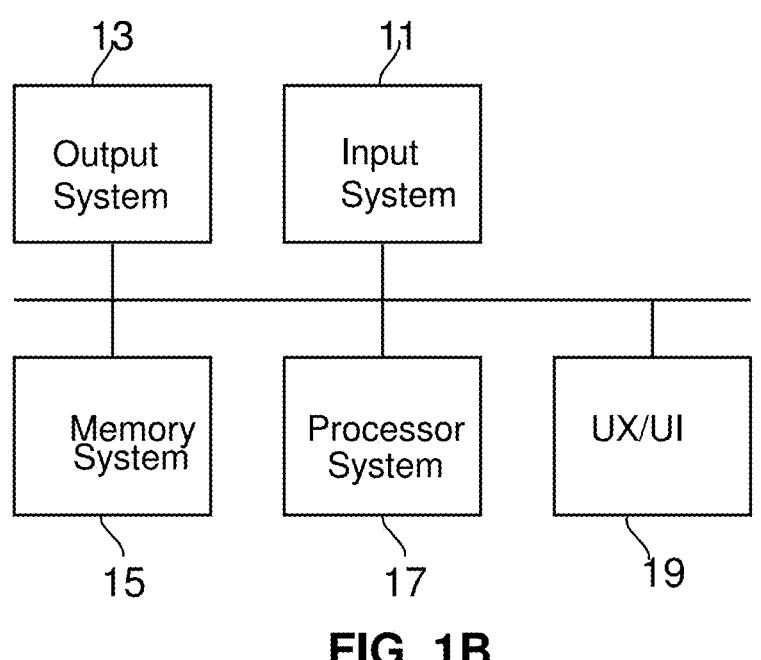
FIG. 1B illustrates a bus diagram of the health interaction mapping system in accordance with an aspect of the invention.

FIG. 1B illustrates an exemplary bus diagram for a system and method for visually mapping medical health codes, including a memory system 15 for storing medical data related to patient interactions and visits, including notes, charts, reports, codes, etc. The processor system 17 is configured to process the stored data and generate a graphical representation of the interaction or visit onto the anatomical map, serving as the first layer of information for the user. Optionally, the first layer may also feature additional information (date of interaction) or an image short-cut directing to the information (interaction details), appearing proximal to the anatomical image on the body graphic of the patient. Optionally, a graphical timeline may appear in the first layer, allowing retrievers an option to access details of varying interactions for the patient in a different layer. In other embodiments, these additional features may be accessed from a different visual layer.

The input system 11 is configured to receive patient data and information related to recent or past interactions/visits, including medical health codes. The output system 13 is configured to present the visual representation of the interaction or visit on the anatomical map, along with the graphical timeline and other visual tools. The UX/UI system 19 is configured to provide an intuitive and interactive interface for the user to navigate through the graphical and informational layers using a pointing device control.

Figure 2:
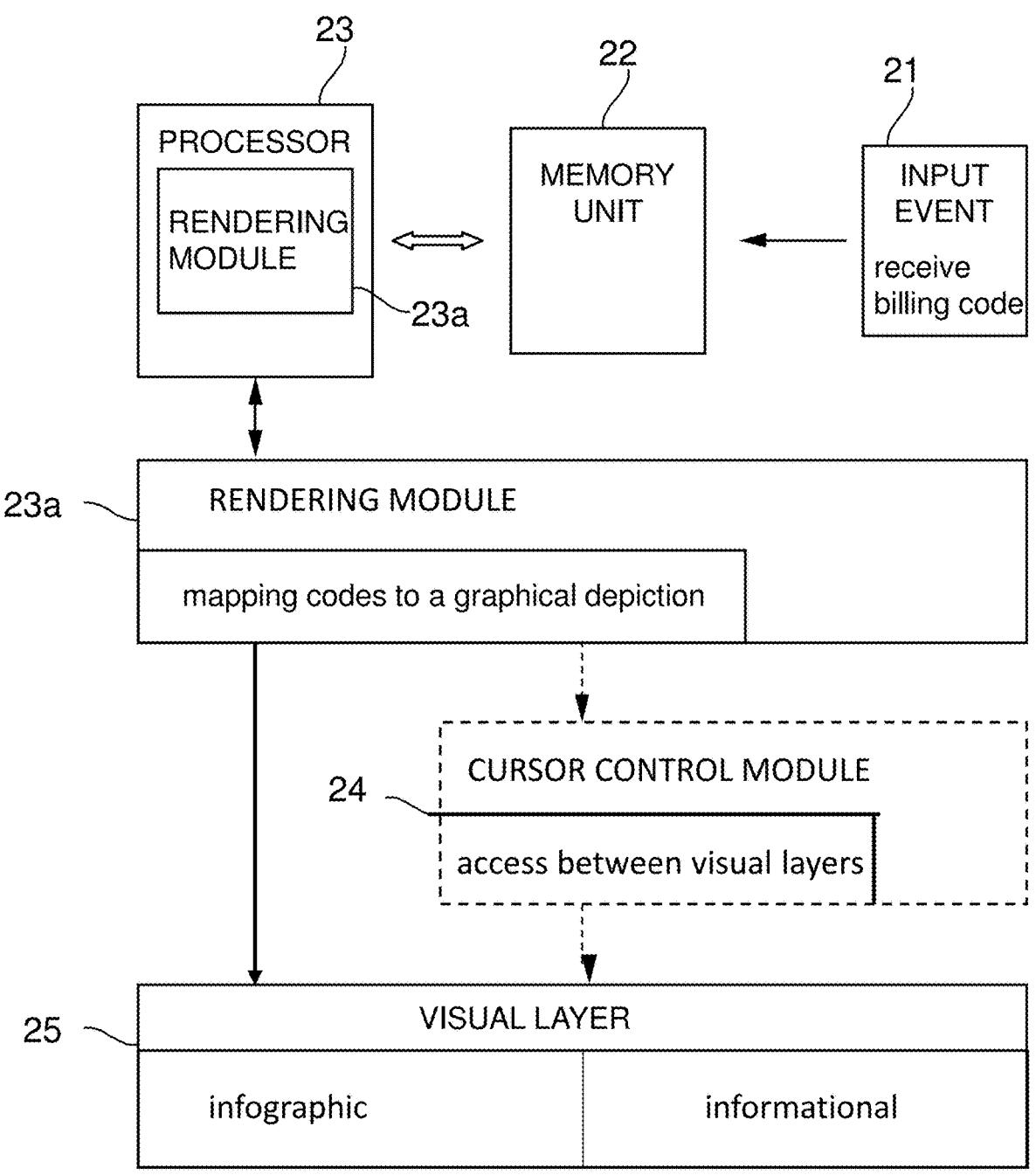
FIG. 2 illustrates a system flow diagram of the health interaction mapping system in accordance with an aspect of the invention.
Figure 3:
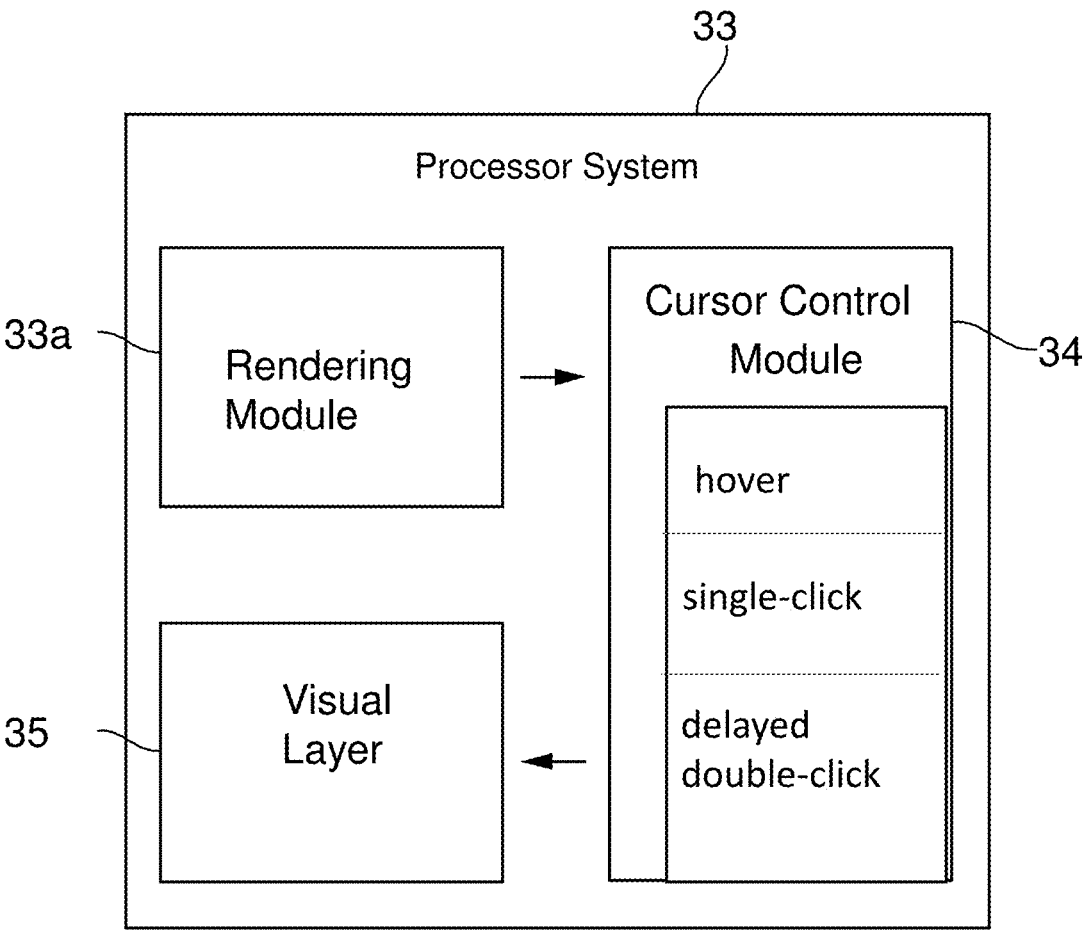
FIG. 3 illustrates a system block diagram of the health interaction mapping system in accordance with an aspect of the invention.
Figure 4:
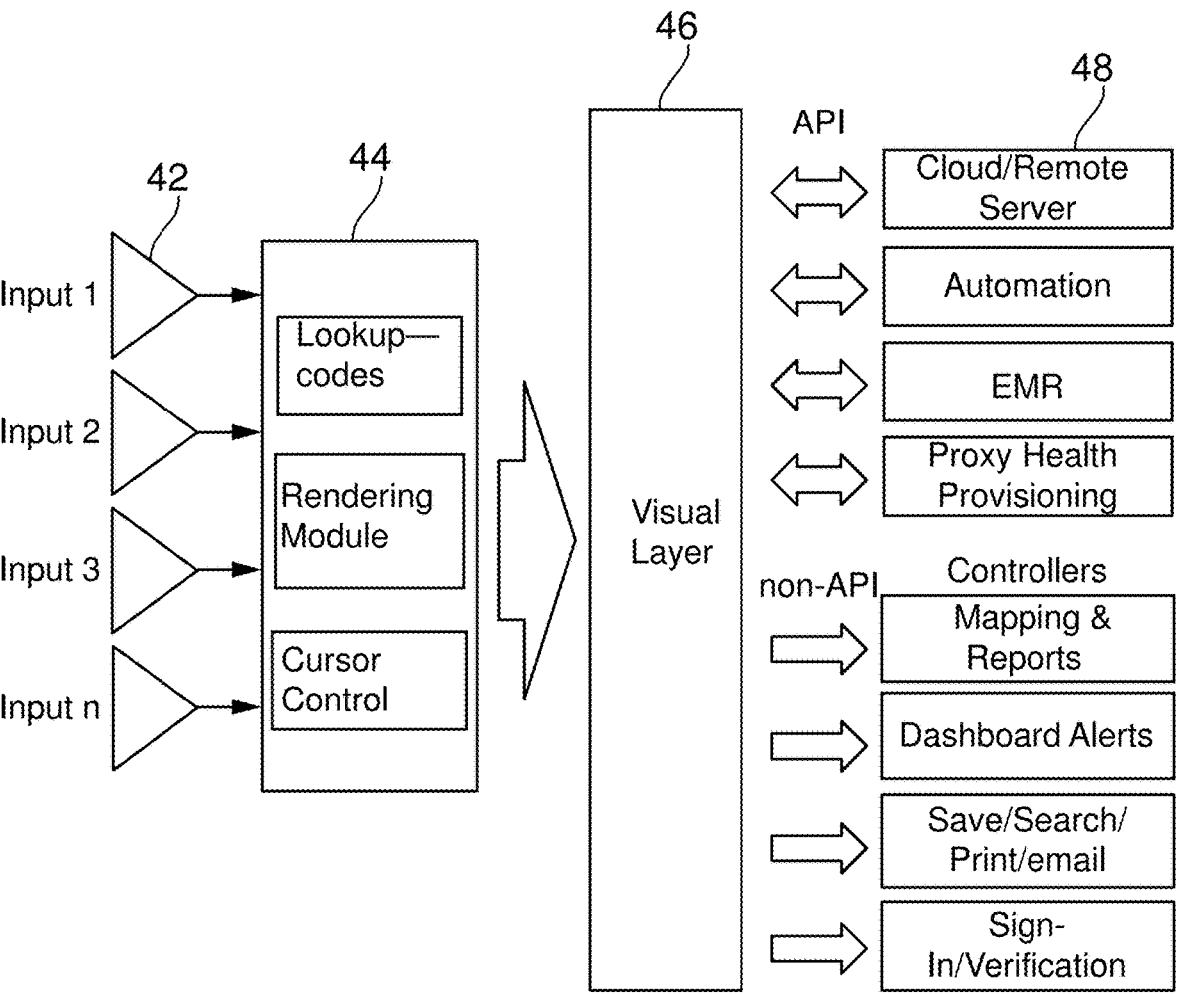
FIG. 4 illustrates an interaction flow diagram of the health interaction mapping system in accordance with an aspect of the invention.

Now in reference to FIGS. 2, 3, and 4, which collectively illustrate an exemplary system flow diagram in accordance with an aspect of the invention. More particularly, FIG. 2 illustrates an exemplary global system interaction, while FIGS. 3 and 4 highlight the processor, detailing individual modules comprised within and, or interacted between. FIG. 2 illustrates a block diagram of the system comprising an input event 21, a memory unit 22 in communication with the input event 21, a processor 23 in communication with the memory unit 22, a processor 23 (further comprising and, or in communication with a rendering module 23a, optionally, a cursor control module, 24 and optionally, a visual layer module 25. In an embodiment, the memory unit 22 is a non-transitory storage element storing encoded information. The encoded instructions when implemented by the processor 23, configure the system to receive information of at least one code implicated from any one of a health code regime with respect to a patients healthcare interaction; match the at least one code with an image representing an anatomy and/or physiology treated during the interaction; and finally render the image of the interaction onto an anatomical map as at least a first layer by the rendering module 23a.

The rendering module 23a correlates the received data, particularly identified health codes, against a stored index of codes and associated anatomical image, retrieving the correlated anatomical image for received code. In one embodiment, the rendering module 23a may use natural language processing or machine learning techniques to identify and extract relevant information from the health code data. The rendering module 23a may then use this information to search the memory unit 22 for an anatomical image (indexed for body map coordinates) that corresponds to the identified code. Once the correlated anatomical image is retrieved, the rendering module 23*a* may then overlay or integrate the image onto the anatomically appropriate coordinates on the body map of the patient, which may be displayed using the visual layer module 25. The cursor control module 24 may allow the user to interact with and manipulate the rendered image on the anatomical map. In other embodiments, the codes may be pre-identified and entered into the system as part of the input event 21, at which point it is matched to an indexed image and projected at the anatomically appropriate coordinates on the patient's body map, as detailed above. It may also be manipulated for visualizing additional data of an informational and, or graphical nature for more efficient retrieval. While not shown in FIG. 2, the system receives the medical health code data through an input event or input stream and matches the health code data against a table of codes tagged with an icon or image of the anatomy associated with the code and 2/3-dimensional coordinate information. The table may be stored in a memory unit or database. Once the match is found, the processor/rendering module would retrieve the corresponding icon or image and render it onto a 2-dimensional human anatomical map featuring the implicated icons/images in their appropriate coordinates on the map.

As shown in FIG. 3, a processor 33/cursor control module 34 may configure the icons or images rendered from the processor 33/rendering module 33*a* to be variably interacted with by specific pointing device controls 34 (hover, single-click, double-click, delayed action), allowing users to access additional informational or visual reveals about the anatomy associated with the health code through a variety of visual layers (informational or graphical) 35. It is to be appreciated by a person of ordinary skill in the art, that any number of pointing device controls may be used, such as voice controls, touch controls, gesture controls, etc.).

FIG. 4 illustrates in a block diagram form, an interaction flow between rendering module, cursor control or pointing device module 44, and the visual layer 46, according to an embodiment. According to an embodiment, the system is configured to receive input data from a plurality of input event sources (providers) 42 and further configured to match the at least one code with an image representing an anatomy and/or physiology treated during the interaction; render the image onto an anatomical map of the patient as a first layer 48 and optionally, access at least a second graphical and/or informational layer for further detail related to the interaction based on a pointing device control (mapping/reports 48). The extracted information based on pointing control variability may be sent to the cloud/remote server, for automation to EMR and to proxy health provisioning 48. In another embodiment, the extracted information may be sent to controllers 48. The controllers 48 includes mapping/ reports, updates, dashboard alerts, export option or store option to save, search, print or email and sign-in/verification unit.

The present invention is a computer-based system that facilitates the interpretation and visualization of medical health codes associated with a patient interaction. The system includes several interconnected modules and features that enable medical professionals to efficiently retrieve and analyze patient data. One of the essential components of the system is a first layer that displays an icon-rich body map of the patient, enabling a retriever to visualize the patient interaction information. Optionally, the map may further comprise time-stamp information of the interaction, along with an icon/code/interaction-identified timeline. In other embodiments, the time-stamp and timeline may be featured in the additional layer (at least second layer). The timestamp, timeline may be previewed from a previous (higher-level) layer (first/map layer) based on a pointing device control (hovering, single-click, prolonged click, double-clicked, etc.). A pointing device control over the icon may route the retriever into a second, graphical and, or informational layer, further detailing the patient interaction in text form, visual form, or any combination thereof.

The graphical/visual layer presents at least one of a textual or numerical description with a related graphic that further details the interaction. This layer can be previewed or quickly reviewed via the pointing device control (preview tile or quick-at-a-glance tile), which can be activated through a variety of means, including hovering, extended press, right or left click, single-click, delayed double-click, touch, extended touch, double-touch, swiped, pinched, hand-gestured, or voice-activated. The pointing device control allows the user to navigate between different layers and retrieve the necessary information efficiently.

The second layer may also comprise an informational layer, or a dedicated layer (third/informational layer) may present at least one of a textual or numerical description without a related graphic further detailing the interaction or event. A preview tile or quick-at-a-glance review tile is provided via the pointing device control for this layer as well. The cursor control of the system enables the user to quick double-click over a preview tile for routing to the corresponding layer, further enhancing the system's ease of use.

To provide more flexibility to the user, the system includes a split screen visual display, wherein each screen represents a different layer, and each screen is modifiable in terms of sizing and position on the screen display. This feature allows the user to adjust the display according to their preferences and work efficiently.

Moreover, the system includes an electronic-discovery tool for tagging the received patient interaction information, making it easier to retrieve and analyze specific information in the future.

Overall, the system's combination of graphical and informational layers, pointing device control, cursor control, split screen visual display, electronic-discovery tool, and anatomical mapping method provides an efficient and user-friendly solution for interpreting and visualizing medical health codes associated with a patient interaction.

Figure 5:
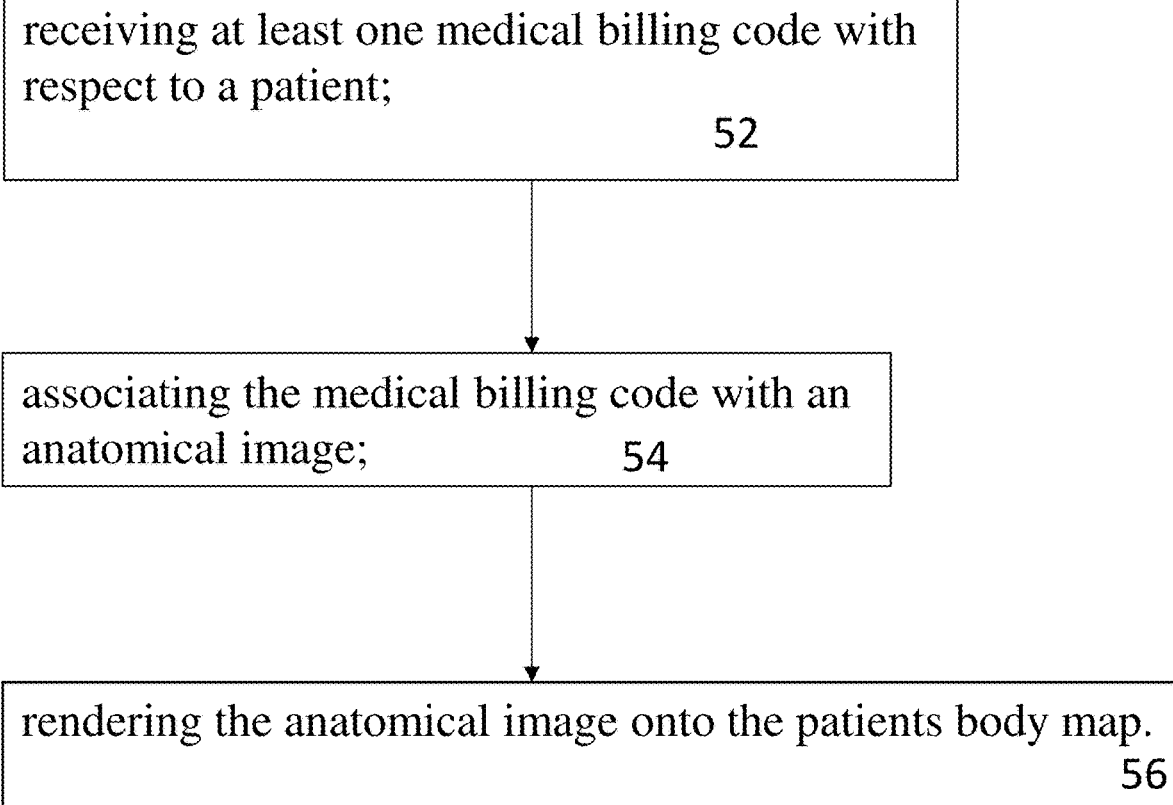
FIG. 5 illustrates a method flow diagram of the health interaction mapping system in accordance with an aspect of the invention.
Figure 6:
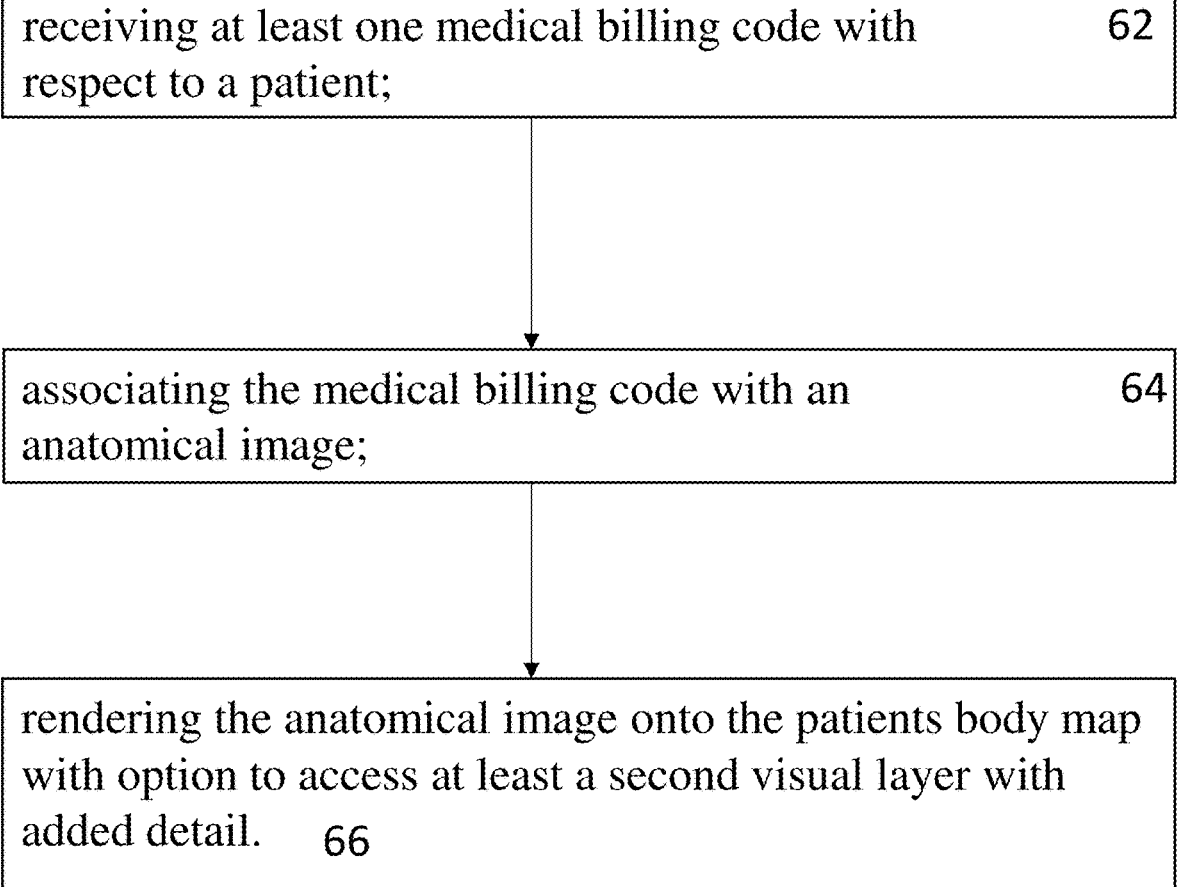
FIG. 6 illustrates a method flow diagram of the health interaction mapping system in accordance with an aspect of the invention.

FIGS. 5 and 6 each illustrate an exemplary method flow diagram of the health code mapping system, comprising the steps of: (1) receiving information of at least one code implicated from any one of a health code regime with respect to a patient healthcare interaction 52, 62; (2) matching the at least one code with an image representing an anatomy and/or physiology treated during the interaction 54, 64; (3) rendering the image of the at least one interaction implicated for the patient onto an anatomical map as a first layer 56, 66; and (optionally) accessing at least a second graphical and/or informational layer for further detail related to the implicated interaction based on a pointing device control 56, 66.

In order to retrieve anatomical images associated with health codes, a processor performs the steps of: correlating received data against a stored index of codes and associated anatomical images (natural language processing/machine learning to extract relevant information from health code data or as a native input event), and then searching the memory unit for an anatomical image indexed for body map coordinates that corresponds to the identified code. Once the correlated anatomical image is retrieved, projecting the image onto the anatomically appropriate coordinates on the patient's body map. The cursor control module allowing the user to manipulate the rendered image on the anatomical map, along with previewing/accessing additional details/visuals/layers. This system may be further enhanced to visualize additional data of an informational and/or graphical nature for more efficient retrieval. The system receives medical health code data through an input event or input stream and matches the health code data against a table of codes tagged with an icon or image of the anatomy associated with the code and 2/3-dimensional coordinate information. This system improves the medical record retrieval process by providing an easy-to-use and easy-to-read graphical interface for quicker and more efficient retrieval of patient data. The visual mapping of medical health codes onto anatomical maps allows users to quickly identify the implicated interaction or visit, and access further details using the graphical and informational layers. This system is suitable for use in claims submission/reimbursal or any other medical retrieval purposes.

Figure 7:
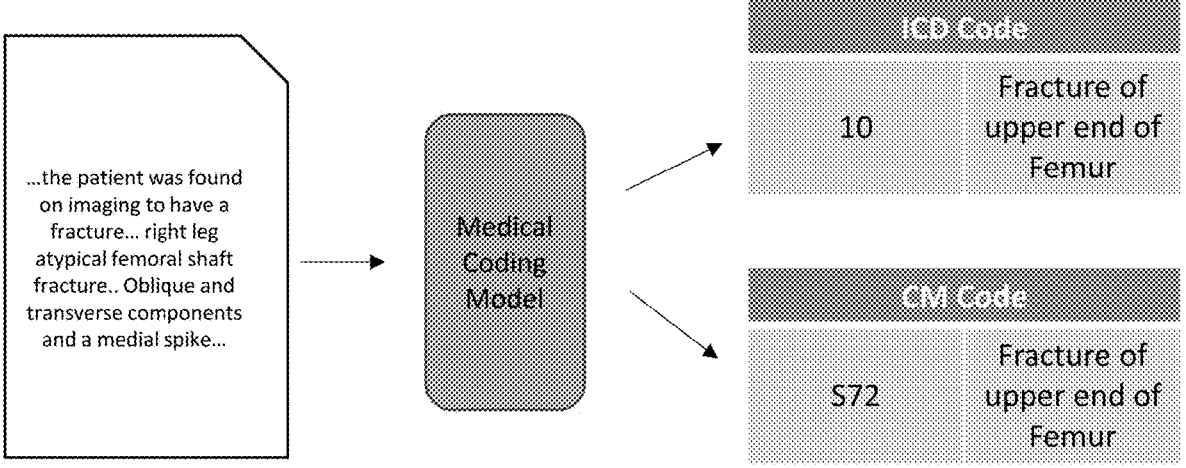
FIG. 7 illustrates a flow diagram of the health interaction mapping system in accordance with an aspect of the invention.
Figure 8:
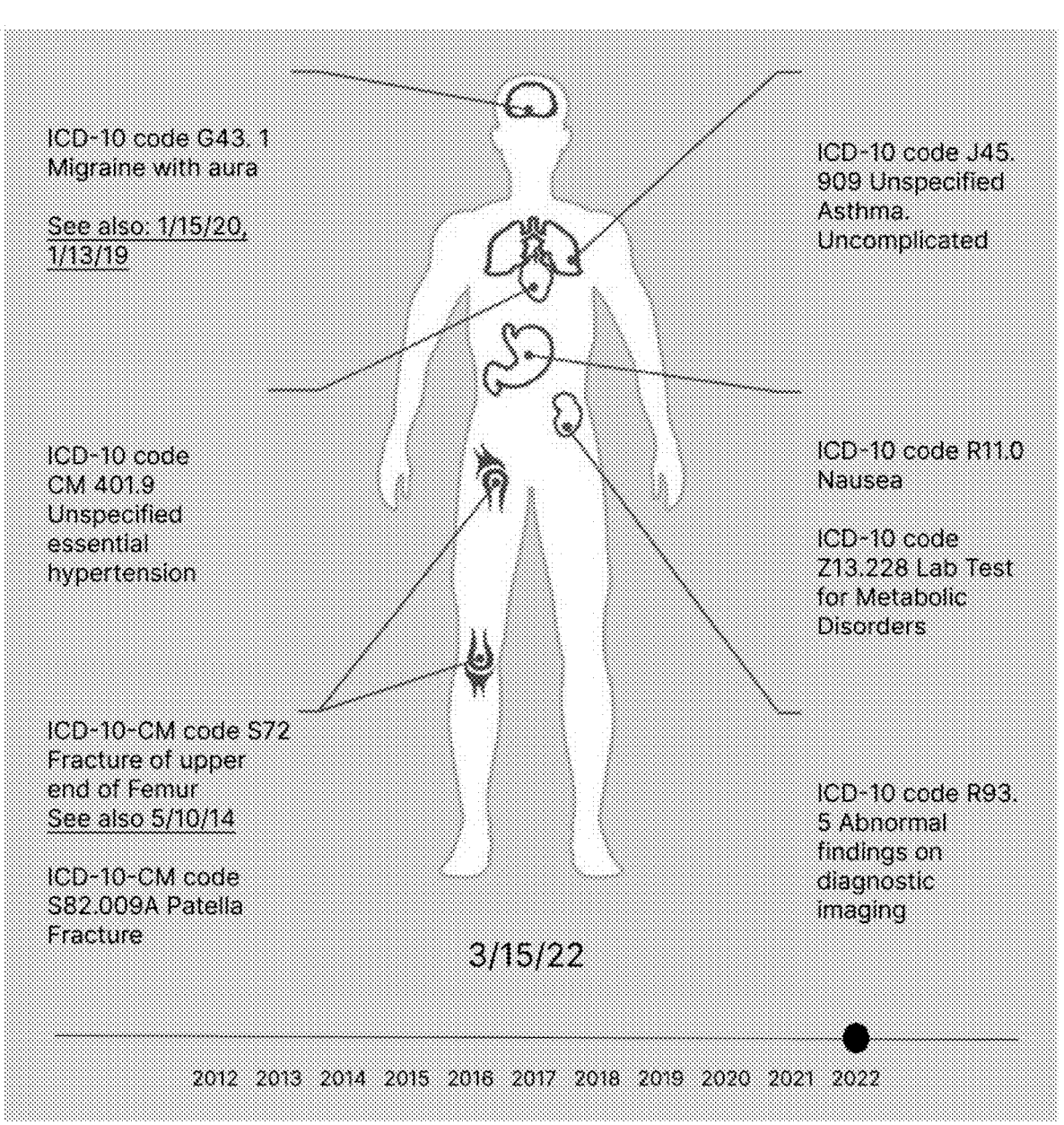
FIG. 8 illustrates an exemplary schematic of the first layer of the health interaction mapping system in accordance with an aspect of the invention.
Figure 9:
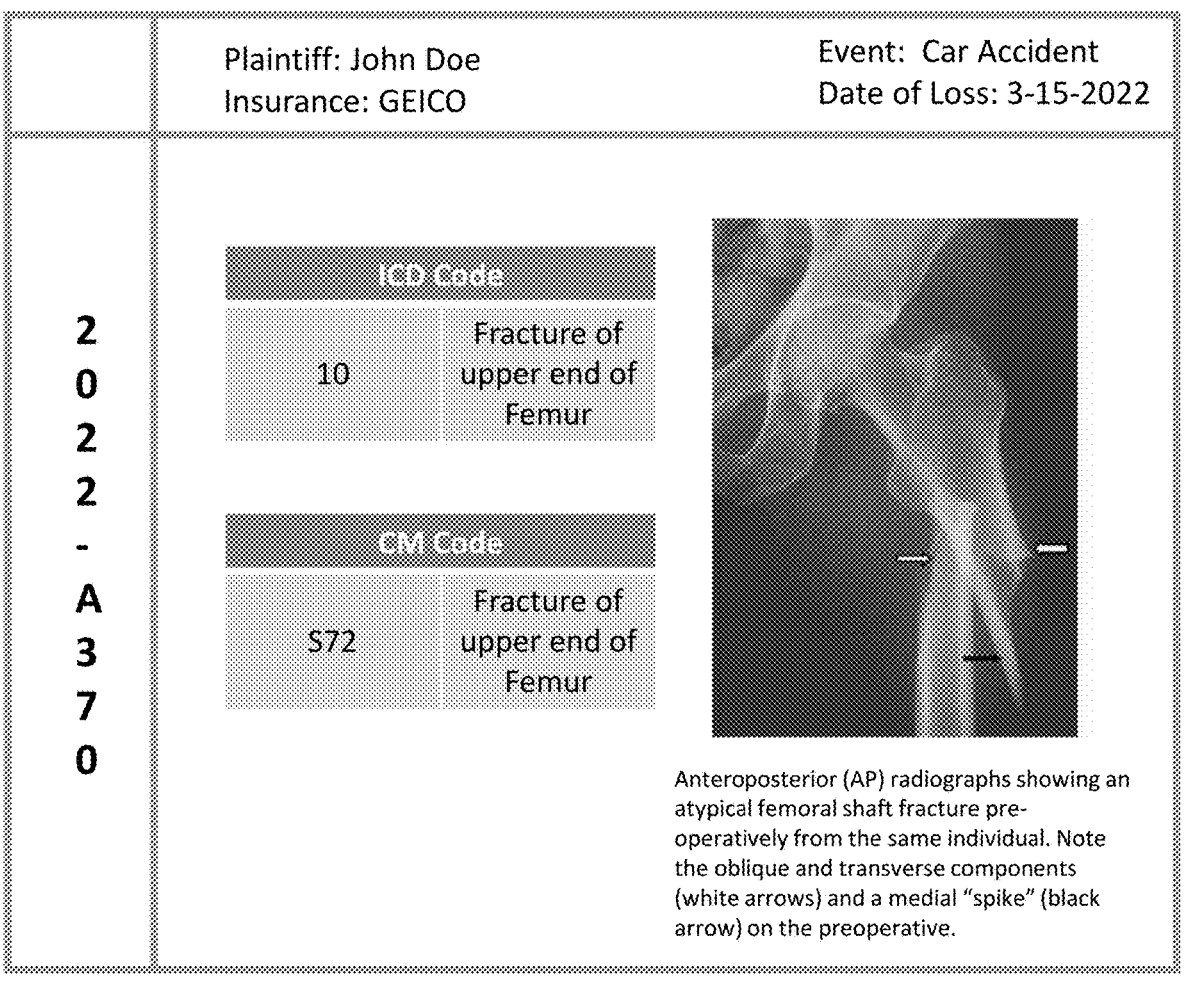
FIG. 9 illustrates an exemplary schematic of at least a second layer of the health interaction mapping system in accordance with an aspect of the invention.

FIG. 7 illustrates a flow diagram of the health interaction mapping system in accordance with an aspect of the invention. FIG. 8 illustrates an exemplary schematic of the first layer of the health interaction mapping system in accordance with an aspect of the invention. FIG. 9 illustrates an exemplary schematic of at least a second layer of the health interaction mapping system in accordance with an aspect of the invention. Finally, FIG. 10 illustrates an exemplary schematic of at least a second layer of the health interaction mapping system in accordance with an aspect of the invention.

In the illustrated situation, an insurance adjuster is examining and summarizing medical records for a patient who was involved in a car accident (upped-end femoral fracture) on Mar. 15, 2022. The medical records are organized using a health interaction mapping system that includes a body graphic layer with a health code and interaction date. This provides the adjuster with a visual representation of the patient's interaction, featuring a timeline of previous interactions (optional). Additionally, the system includes multiple layers with more detailed information such as x-rays and laboratory reports.

To interact with the system, the adjuster can use pointing device controls like hovering, pressing, or clicking, to access and interact with standardized data related to the patient interaction. The adjusters access to the patient interaction is hierarchical, based on the pointing device controls. By selecting the imagery on the body graphic layer, the adjuster can access at least one of a second visual or informational layer that depicts the patient interaction.

During the review, the adjuster clicked on the prior interaction notification with a date-stamp on the body graphic layer (5/10/14), which routed the adjuster to a detailed visual/graphical layer of the patient's previous interaction. The previous interaction registered the same health code (ICD-10-Code S72) and implicated the anatomy (upper-end femur) at issue of the Mar. 15, 2022 interaction and the basis of the current claim. After reviewing the previous interaction, the adjuster determined that a precondition exists with respect to the upper end femoral fracture sustained during the Mar. 15, 2022 car accident and denied the claim.

Although not shown in FIGS. 8-10, the system may also feature a split-screen visual display, electronic discovery tools for tagging, annotating, coding, and sharing received patient interaction information, as well as the ability to compile or submit pertinent information to relevant parties. Overall, the system streamlines the adjuster's—and other actors in the medical record review system—claims processing (and other record review functions) by organizing and presenting medical records in a visual and hierarchical manner.

The figures illustrate the architecture, functionality, and operation of possible implementations of systems, methods and computer program products according to various embodiments of the present invention. It should also be noted that, in some alternative implementations, the functions noted/illustrated may occur out of the order noted. For example, two blocks shown in succession may, in fact, be executed substantially concurrently, or the blocks may sometimes be executed in the reverse order, depending upon the functionality involved.

Since various possible embodiments might be made of the above invention, and since various changes might be made in the embodiments above set forth, it is to be understood that all matter herein described or shown in the accompanying drawings is to be interpreted as illustrative and not to be considered in a limiting sense. Thus, it will be understood by those skilled in the art of creating independent multilayered virtual workspace applications designed for use with independent multiple input systems that although the preferred and alternate embodiments have been shown and described in accordance with the Patent Statutes, the invention is not limited thereto or thereby.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some portions of embodiments disclosed are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media (e.g., read-only memory devices within a computer such as CD-ROM disks readable by a CD-ROM drive); (ii) alterable information stored on writable storage media (e.g., floppy disks within a diskette drive or hard-disk drive, solid-state disk drive, etc.); and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

I claim:

1. A method for anatomically mapping a medical health code, said method comprising the steps of:

receiving one or more medical health codes associated with a patient interaction;

associating the one or more medical health codes with a corresponding anatomical image selected from a library of anatomical images;

rendering on a first visual layer comprising a patient body map overlaid with the anatomical images associated with each of the medical health codes displayed on the first visual layer in a manner to correspond with the anatomical images; and in response to a user performing pointing device control with the first visual layer, generating at least a second graphical and/or informational visual layer that displays additional information associated with the medical health code, the additional information comprising:

(i) the medical health code displayed in visual association with at least one radiographic, photographic, or diagnostic image corresponding to the medical interaction; and (ii) insurance-adjusting or litigation-related information associated with the medical interaction, including both clinical and non-clinical information, wherein the non-clinical information comprises at least one of claimant or plaintiff identification, insurance carrier identification and event or loss information, and wherein the clinical information comprises diagnostic and anatomical information corresponding to the medical health code.

2. The method of claim 1, wherein the one or more medical health codes are any alphanumeric code, translating the a-patient interaction for review, including a classification of the patient interaction.

3. The method of claim 1, wherein the patient interaction is at least one of an encounter, diagnosis, procedure performed, test performed, prescriptions, device-collected data, devices, or supplies provided to the patient.

4. The method of claim 1, wherein associating the one or more medical health codes with a corresponding anatomical image is performed by a code matched to an anatomical image tagged with at least one code with map-coordinate information for rendering the image and code information onto the body map for further interaction.

5. The method of claim 1, wherein the first visual layer further comprises a time-stamp of the interaction.

6. The method of claim 1, wherein the first visual layer further comprises a time-line of previous interactions.

7. The method of claim 1, wherein the second visual layer presents at least one of a textual or numerical description with a related graphic further detailing the patient interaction.

8. The method of claim 7, wherein the second visual layer may be previewed or quick-at-a-glance reviewed via the pointing device control.

9. The method of claim 8, wherein the pointing device control is at least one of hovering, extended press, right or left click, single-click, delayed double-click, touch, extended touch, double-touch, swiped, pinched, hand-gestured, or voice-activated.

10. The method of claim 1, wherein the at least second visual layer presents at least one of a textual or numerical description without a related graphic further detailing the patient interaction.

11. The method of claim 8, wherein the pointing device control including for at least one of hovering, extended press, right or left click, single-click, delayed double-click, touch, extended touch, double-touch, swiped, pinched, hand-gestured, or voice-activated for a preview tile or quick-at-a-glance review tile.

12. The method of claim 11, further comprising a cursor control enabling a user to quick double-click over the preview tile for routing to at least one of the second visual layer.

13. The method of claim 1, further comprising a split screen visual display, wherein each screen represents a different layer and each screen modifiable in terms of sizing and position on the screen display.

14. The method of claim 1, further comprising at least one of an electronic-discovery tool for tagging, annotating, coding, or sharing the received patient interaction information.

15. A system for generating an interactive body map of a patient medical history, said system comprising:

a processor;

a non-transitory storage element coupled with the processor for storing encoded instructions;

wherein the encoded instructions, when implemented by the processor, configure the system to:

receive one or more medical health codes associated with a patient interaction;

associate the one or more medical health codes with a corresponding anatomical image selected from a library of anatomical images;

render on a first visual layer comprising a patient body map overlaid with the anatomical images associated with each of the medical health codes displayed on the first visual layer in a manner to correspond with the anatomical images; and in response to a user performing pointing device control with the first visual layer, generating at least a second graphical and/or informational visual layer that displays additional information associated with the medical health code, the additional information comprising:

(i) the medical health code displayed in visual association with at least one radiographic, photographic, or diagnostic image corresponding to the medical interaction; and (ii) insurance-adjusting or litigation-related information associated with the medical interaction, including both clinical and non-clinical information, wherein the non-clinical information comprises at least one of claimant or plaintiff identification, insurance carrier identification and event or loss information, and wherein the clinical information comprises diagnostic and anatomical information corresponding to the medical health code.

* * * * *